US010932692B2

(12) United States Patent
Kertser

(10) Patent No.: US 10,932,692 B2
(45) Date of Patent: Mar. 2, 2021

(54) PRONG-FREE CANNULA DEVICE FOR $CO_2$ SAMPLING AND $O_2$ DELIVERY

(71) Applicant: ORIDION MEDICAL 1987 LTD., Jerusalem (IL)

(72) Inventor: Michael Kertser, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 481 days.

(21) Appl. No.: 15/868,536

(22) Filed: Jan. 11, 2018

(65) Prior Publication Data

US 2018/0192915 A1 Jul. 12, 2018

Related U.S. Application Data

(60) Provisional application No. 62/445,515, filed on Jan. 12, 2017.

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *A61B 5/0836* (2013.01);
(Continued)

(58) Field of Classification Search
CPC ..... A61B 5/097; A61B 5/0836; A61B 5/6819; A61B 5/082; A61M 16/1005;
(Continued)

(56) References Cited

U.S. PATENT DOCUMENTS

2007/0272247 A1 11/2007 Porat
2008/0190436 A1* 8/2008 Jaffe ................. A61M 16/0051
128/207.18
(Continued)

FOREIGN PATENT DOCUMENTS

WO 2006130369 A2 12/2006
WO WO-2006130369 A2 * 12/2006 .......... A61M 16/202

OTHER PUBLICATIONS

International Search Report and Written Opinion for PCT Application No. PCT/US2018/013585 dated Mar. 29, 2018, 14 pgs.

*Primary Examiner* — Navin Natnithithadha
*Assistant Examiner* — Andrey Shostak
(74) *Attorney, Agent, or Firm* — Cantor Colburn LLP

(57) ABSTRACT

A gas flow-focusing device (FFD) may include a cylindrical body that may include a funneling part to receive exhaled CO2-enriched air, and a CO2 sampling part. The CO2 sampling part and the funneling part are in fluid flow communication. The CO2 sampling part may include a CO2 sampling chamber to accept the CO2-enriched air, and a CO2 sampling tube to sample the CO2-enriched air. The funneling part and the CO2 sampling part may structurally form between them a ring-shaped gas chamber to contain a pressurized propellant gas, and a hollow channel in order to channel the pressurized propellant gas from the gas chamber to the CO2 sampling chamber. The gas chamber may include a gas intake opening through which propellant gas may fill the gas chamber. A prong-free cannula (PFC) may include two FFDs for sampling CO2, and a plurality of apertures for providing, there through, oxygen.

21 Claims, 11 Drawing Sheets

(51) Int. Cl.

| | |
|---|---|
| *A61M 16/06* | (2006.01) |
| *A61M 16/22* | (2006.01) |
| *A61M 16/08* | (2006.01) |
| *A61B 5/083* | (2006.01) |
| *A61B 5/00* | (2006.01) |
| *A61M 16/10* | (2006.01) |

(52) U.S. Cl.
 CPC ....... *A61B 5/6819* (2013.01); *A61M 16/0672* (2014.02); *A61M 16/085* (2014.02); *A61M 16/1005* (2014.02); *A61M 16/22* (2013.01); *A61M 2202/0208* (2013.01); *A61M 2206/20* (2013.01); *A61M 2230/432* (2013.01)

(58) Field of Classification Search
 CPC .............. A61M 16/0672; A61M 16/22; A61M 16/085; A61M 2202/0208; A61M 2230/432; A61M 2206/20
 See application file for complete search history.

(56) References Cited

U.S. PATENT DOCUMENTS

| | | | |
|---|---|---|---|
| 2010/0113955 A1* | 5/2010 | Colman | A61M 16/0666 600/532 |
| 2011/0214676 A1* | 9/2011 | Allum | A61M 16/0672 128/207.18 |
| 2015/0208953 A1* | 7/2015 | Levitsky | A61M 16/085 600/543 |
| 2016/0074615 A1 | 3/2016 | Beard | |

* cited by examiner

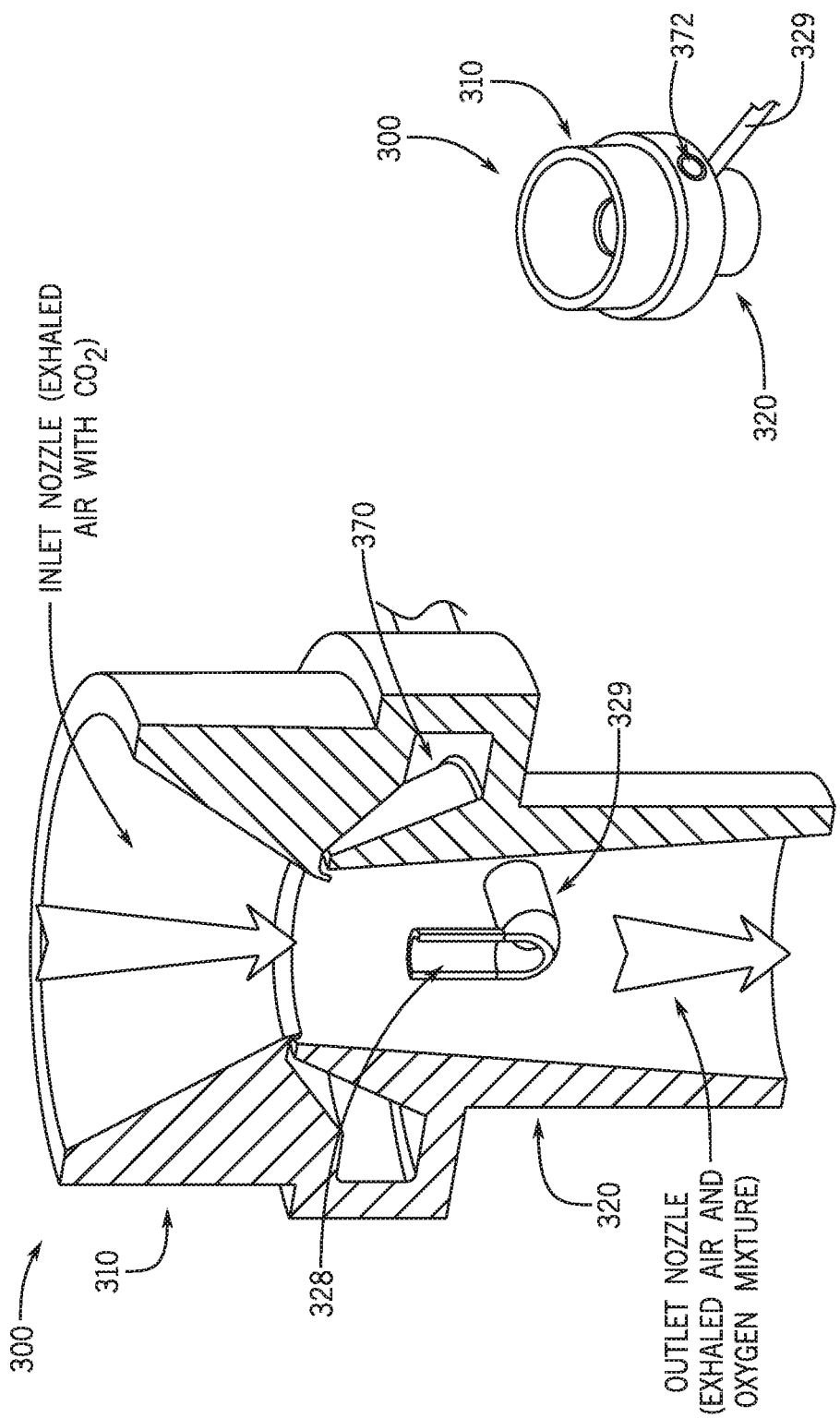

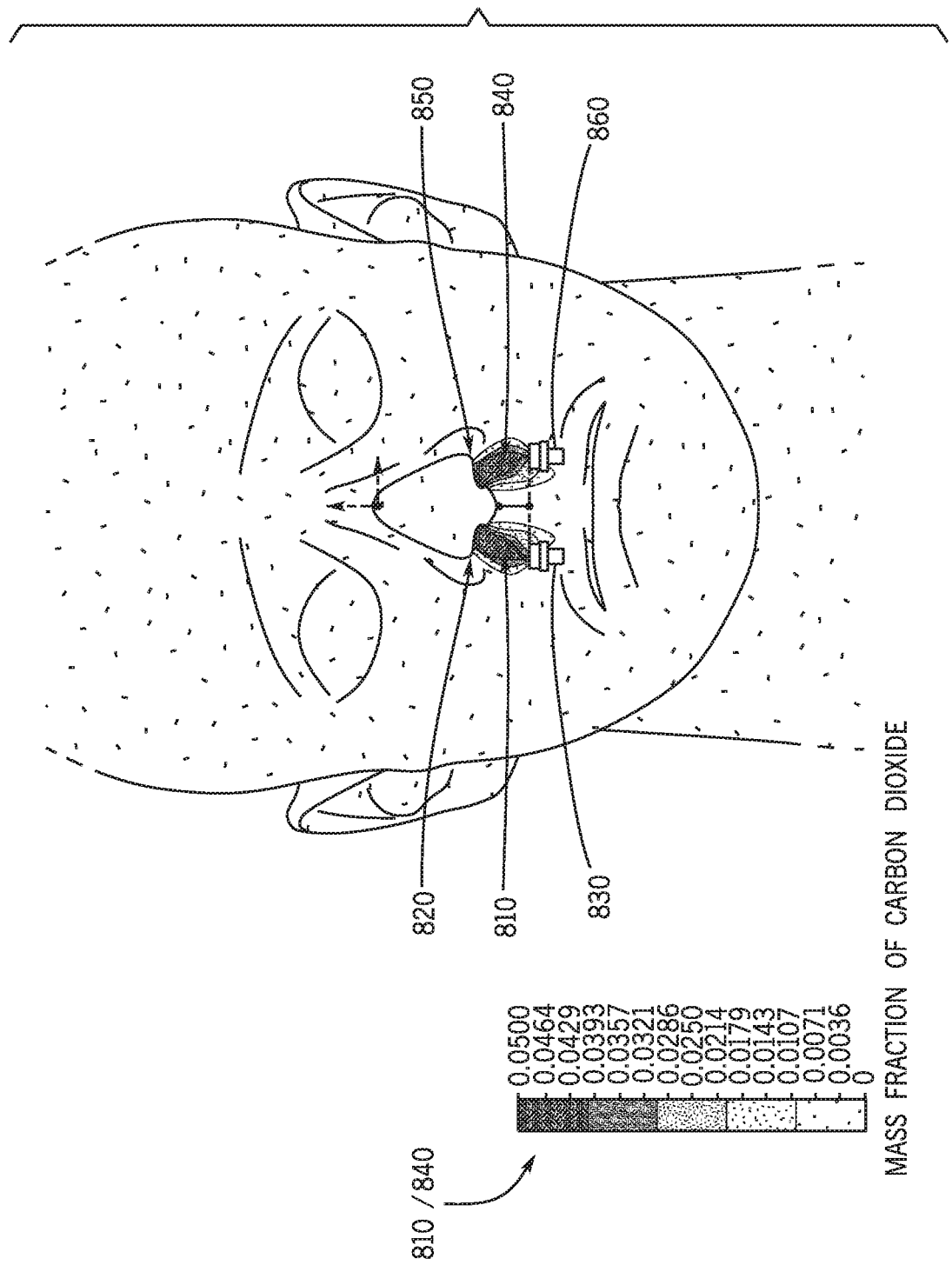

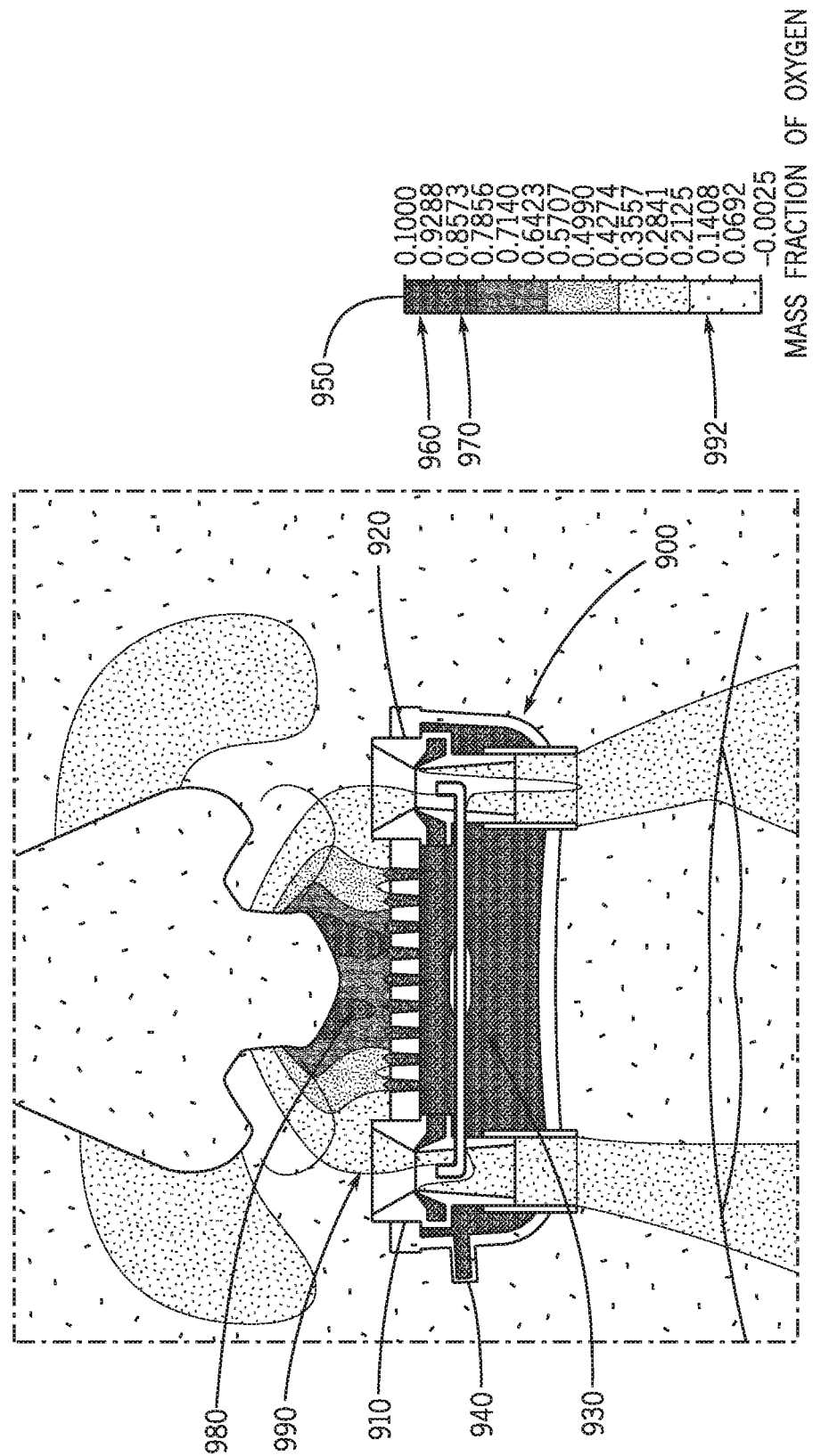

PRONG-FREE CANNULA DEVICE FOR $CO_2$ SAMPLING AND $O_2$ DELIVERY

This application claims the benefit of U.S. Provisional Application Ser. No. 62/445,515 filed Jan. 12, 2017, the content of which is incorporated herein by reference in its entirety for all purposes.

TECHNICAL FIELD

The present disclosure generally relates to a capnography cannula for sampling exhaled carbon dioxide ($CO_2$), and more specifically to a prong-free cannula that allows sampling of $CO_2$ that is exhaled by a subject and transfer of oxygen to the subject.

BACKGROUND

There exist various nasal-oral cannula devices. While the primary function of an oxygen cannula is providing oxygen to patients who need it, advanced oxygen cannulas with capnometric capability still include nasal prongs that need to be pushed deep inside the patient nostrils in order to achieve an acceptable $CO_2$ measurement with no significant oxygen dilution and gas dispersion.

However, certain nasal prongs have drawbacks. For example, nasal prongs are generally uncomfortable and may cause irritation and itchiness of patient's skin. Accordingly, nasal prongs may be a source of annoyance to most patients since, among other things, the nasal geometry differs from patient to patient. Additionally the cannula prongs are, in general, designed in one size to fit average anthropometrical values of nose/nasal geometry.

PRIOR ART FIG. 1A depicts a nasal cannula with two prongs (100), one prong per nostril, for providing oxygen to a subject. PRIOR ART FIG. 1B depicts a nasal cannula 110 with two prongs, which are shown inserted into nose 120, and an oral scoop 130. The cannula 110 allows both sampling CO.sub.2 from and delivering oxygen to the patient's airway. PRIOR ART FIG. 10 depicts a cannula that includes a nasal prong for sampling CO.sub.2 (cannula prong 140), a nasal prong for delivering oxygen (cannula prong 150), and an internal septum that separates the two prongs.

While sampling $CO_2$ and delivering oxygen are beneficial, there are some drawbacks associated with cannulas that include prongs, as specified above. It would be, therefore, advantageous to have a bi-functional cannula that does not use nasal prongs and, yet, allows both sampling $CO_2$ (e.g., facilitate measuring $EtCO_2$ values) with high confidence (e.g., ±4 mmHg) and delivering oxygen at desirable oxygen flow rates, for example at oxygen flow rates up to 10 liters per minute (LPM).

SUMMARY

Disclosed herein is a gas flow-focusing device ("FFD") for sampling exhaled gases from a patient's airway. The FFD may include a funneling part that is configured to receive and funnel exhaled $CO_2$-enriched air, and a carbon oxide ($CO_2$) sampling part that is in fluid flow communication with the funneling part. The $CO_2$ sampling part may include a $CO_2$ sampling chamber to receive the $CO_2$-enriched air, and a $CO_2$ sampling tube located in the $CO_2$ sampling chamber to evacuate a $CO_2$ sample from the $CO_2$ sampling chamber to the outside of the FFD. The $CO_2$ sampling tube may include an axial $CO_2$ tube section that may be centered in the $CO_2$ sampling chamber. The funneling part and the $CO_2$ sampling part may have a common longitudinal axis (e.g., coaxial) and form a gas chamber between them, to contain a propellant gas, and a hollow channel to channel the propellant gas from the gas chamber into and through the $CO_2$ sampling chamber. The $CO_2$ sampling part may further include a gas exhaust section.

Each of the funneling part and the $CO_2$ sampling part may include an 'L'-shaped mounting member. The $CO_2$ sampling part may include a cylindrical body, and the 'L'-shaped mounting member of the $CO_2$ sampling part and the cylindrical body may jointly form a ring-like channel. The cylindrical body of the $CO_2$ sampling part comprises a tapering end. The funneling part may include a conical hollow space that is configured to mate with the tapering end of the $CO_2$ sampling part, to thus form the hollow channel.

The funneling part may include an after-funneling extension ("AFE") that may protrude into the $CO_2$ sampling chamber. The AFE may form a circular outlet opening for the hollow channel, so that a gas flowing from the gas chamber flows into the $CO_2$ sampling chamber in the form of a gas jet.

Also disclosed herein is a prong-free cannula ("PFC"). The PFC may include a first gas flow-focusing device and a second gas flow-focusing device to sample $CO_2$-enriched air exhaled by a subject. The PFC may also include a cannula body that may include the first gas flow-focusing device, the second gas flow-focusing device, and, in addition (as an option), a plurality of apertures for providing, there through, oxygen to a subject during inhalation. Each of the first gas flow-focusing device and the second gas flow-focusing device may include the elements described herein.

The PFC may also include a $CO_2$ sampling line that may be connected to the $CO_2$ sampling tube of each of the first and second gas flow-focusing devices, and, in addition, an oxygen manifold that is in fluid flow communication with the plurality of apertures and with the gas chamber of (in) each gas flow-focusing device. The $CO_2$ sampling line may connect each $CO_2$ sampling tube of the FFDs to an external $CO_2$ monitoring system. The PFC may be used only for sampling exhaled $CO_2$, or only for providing oxygen to a subject, or for both functions. The PFC may also include an oxygen line for providing oxygen both to the plurality of apertures and to the gas intake opening of the gas chamber of (in) each FFD.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

PRIOR ART

PRIOR ART

PRIOR ART

FIG. 3A depicts a cross-sectional view of a three-dimensional FFD according to an example embodiment;

FIG. 3B depicts the FFD of FIG. 3A in full, from a different perspective;

FIG. 8 depicts simulated $CO_2$ flow from a subject's nose towards, and around, two FFDs according to an example embodiment;

FIG. 9 depicts simulated oxygen flow from a prong-free cannula towards subject nostrils according to an example embodiment; and FIG. 10 depicts simulation of $CO_2$ flow from two nostrils to two FFD according to an example embodiment.

DETAILED DESCRIPTION OF THE INVENTION

Figure 1B:
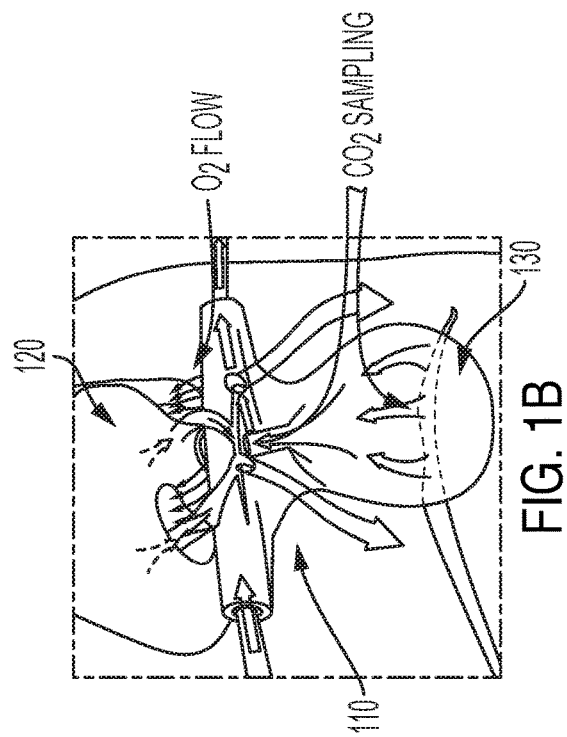
FIG. 1B depicts a cannula with prongs and an oral scoop.
Figure 1C:
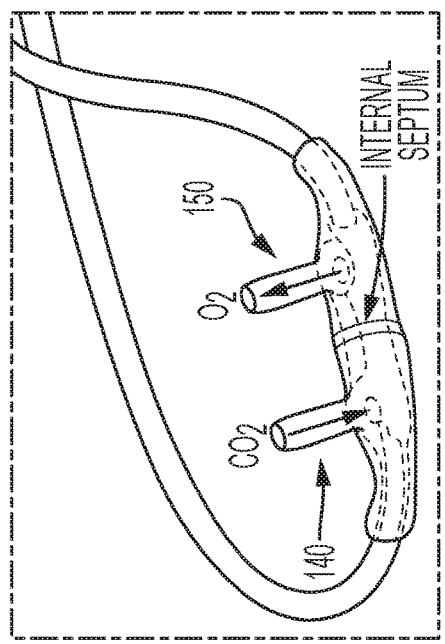
FIG. 1A depicts a cannula with prongs.
Figure 1A:
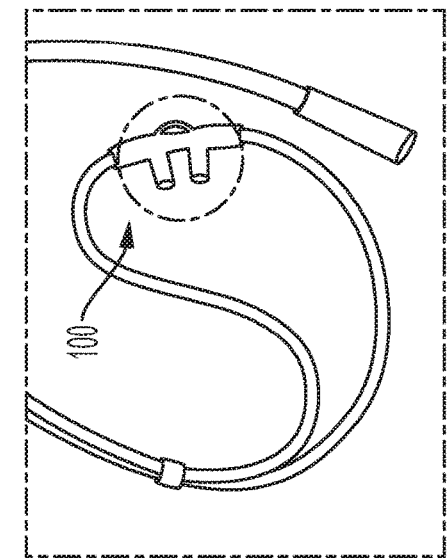

The description that follows provides various details of exemplary embodiments. However, this description is not intended to limit the scope of the claims but instead to explain various principles of the disclosure and the manner of practicing it.

In the following description, various aspects of the disclosure will be described. For purposes of explanation, specific configurations and details are set forth in order to provide a thorough understanding of the disclosure described herein. However, it will also be apparent to one skilled in the art that the disclosure may be practiced without the specific details presented herein. Furthermore, well-known features may be omitted or simplified in order not to obscure the disclosure.

Herein is described a new $CO_2$ FFD for capturing and providing samples of exhaled $CO_2$ (exhaled $CO_2$-enriched air) to a $CO_2$ sampling tube (for measuring $CO_2$ concentration by an external, or a remote, $CO_2$ monitoring system). The FFD utilizes two fluid dynamics properties, one of which is a fluid dynamics property called the "Coanda effect," and the other fluid dynamics property is called the "Venturi effect." Briefly, the Coanda effect is a phenomena in which a fluid jet flow attaches itself to a nearby surface and remains attached to the surface even if the surface curves away from the initial direction of the jet. Briefly, the Venturi effect involves reduction in a fluid static pressure as a result of a fluid flowing through a constricted section of a pipe. The FFD utilizes the two fluid dynamics properties simultaneously in order to increase the efficiency of $CO_2$ sampling: a propellant gas is forced to flow into the FFD in order to reduce a static pressure inside the FFD (per the Venturi effect) in order to draw, into the FFD, more $CO_2$-enriched air than would have been otherwise possible. At the same time, the Coanda effect ensures separation between the propellant gas and the $CO_2$-enriched air in a '$CO_2$ sampling chamber' inside the FFD, such that the two types of gases do not mix up in the $CO_2$ sampling chamber in the FFD. Separation between the propellant gas and the $CO_2$ in the $CO_2$ sampling chamber in the FFD is essential in order to decrease, and in certain embodiments prevent, dilution of the $CO_2$ sample by the propellant gas. In other words, while the propellant gas draws exhaled $CO_2$-enriched air into the FFD, it does not mix with the gas (e.g., $CO_2$) subject of the sampling. As shown in the accompanying drawings and described herein, the FFD is designed in a way that allows the utilization of the two fluid dynamics properties.

In general, the FFD includes two main parts: (1) a funneling part, and (2) a $CO_2$ sampling part. The funneling part is configured to channel $CO_2$ to the $CO_2$ sampling part. The $CO_2$ sampling part is configured such that it allows a propellant gas to flow through it, in compliance with the Coanda effect, in a way that actively draws $CO_2$ (or $CO_2$-enriched air) from the exhaled $CO_2$ into a $CO_2$ sampling tube that resides in the $CO_2$ sampling part.

Also described herein is a PFC that has a cannula body that includes two FFDs (one FFD for each nostril). The PFC may include only two FFDs in order to sample exhaled $CO_2$, or only a plurality of apertures for provide oxygen to the subject wearing the PFC, or both FFDs and apertures.

The PFC device may be used to sample exhaled $CO_2$ or any other gas (for example metabolic waste related to cellular respiration, a gas indicative of or characterizing a physiological condition of a subject or a pathology, etc.) that a subject may exhale. In some embodiments, both FFDs are used to sample the same type of gas (e.g., $CO_2$, etc.), which means that a gas sampling tube may channel gas samples from the respective FFD to a different gas monitoring system. In other embodiments, each FFD is used to sample a different type of gas, which means that a first gas sampling tube may channel gas samples from a first FFD to a first gas monitoring system, and a second gas sampling tube may channel gas samples from a second FFD to a second, different, gas monitoring system. In addition, the propellant gas may be a gas other than oxygen.

Figure 2A:
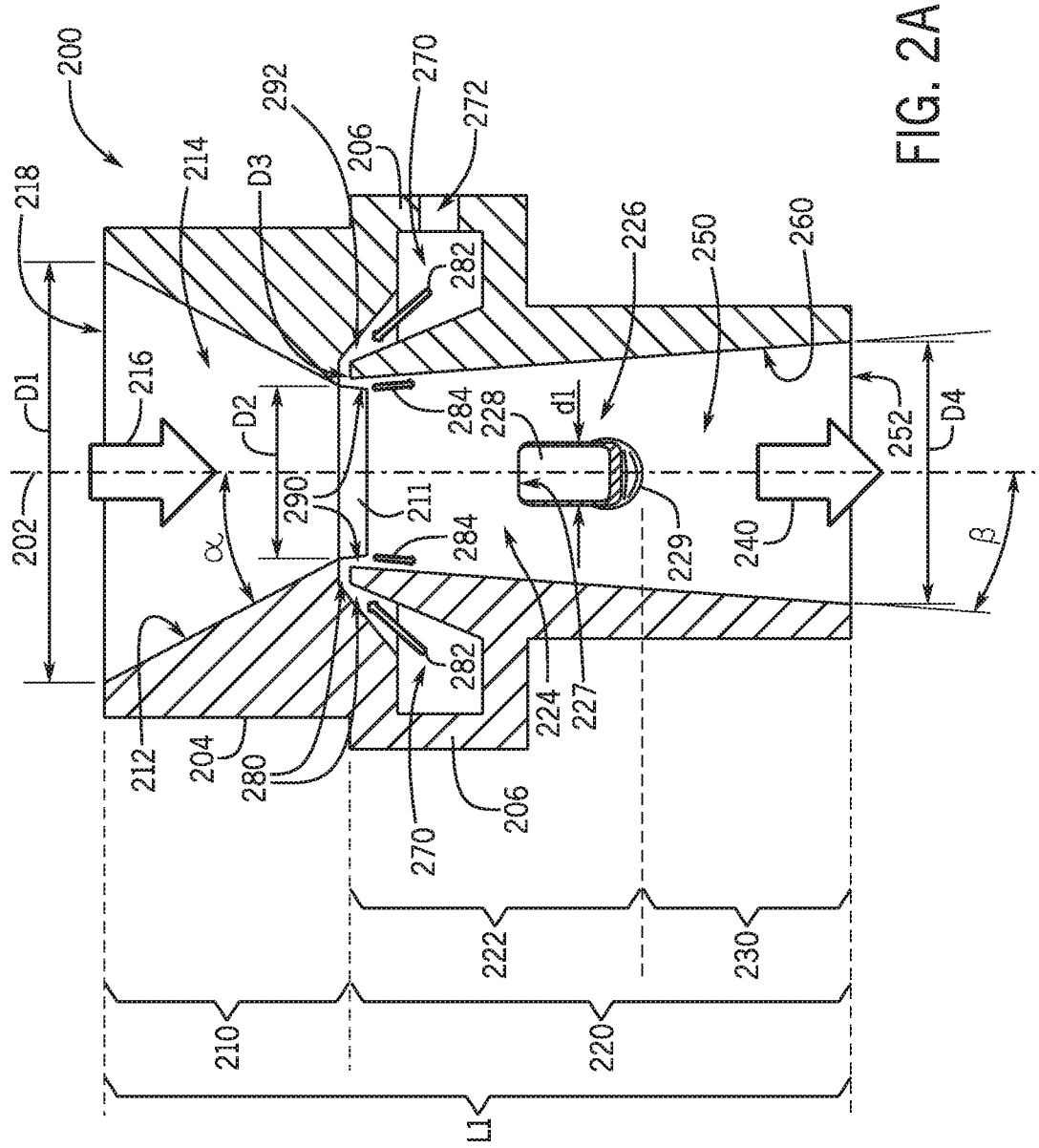
FIG. 2A shows a cross-sectional view of a flow-focusing device (FFD) according to an example embodiment.

FIG. 2A shows a cross-sectional view of a FFD 200 according to an example embodiment. The FFD 200 has a rounded body 204 that may generally be cylindrical. The body of the FFD 200 may have a geometric shape different than cylinder. The FFD 200 may include two main parts that may be positioned lengthwise both structurally and functionally: (1) a funneling part 210, and (2) a $CO_2$ sampling part 220. The funneling part 210 and the $CO_2$ sampling part 220 may form or be manufactured as one device with a longitudinal axis 202. Alternatively, the funneling part 210 and the $CO_2$ sampling part 220 may be separate devices that are mounted to one another or on one another such that they have the same longitudinal axis (e.g., axis 202). Each of the funneling part 210 and the $CO_2$ sampling part 220 may have a different longitudinal axis, and the two longitudinal axes may be at an angle (e.g., 10 degrees) with respect to one another. For example, the $CO_2$ sampling part (220), or only the exhaust section (230), may be at angle with respect to the longitudinal axis of the funneling part (210).

The funnel part 210 may include an internal conical cylinder (tapering) 'funneling' surface 212 that forms a truncated conical hollow 214 ('frustum' hollow or cavity) that passes through the funnel part 210 and functions as an intake nozzle. $CO_2$-enriched air that is exhaled by a subject through one of her/his nostrils during breathing (and flows in direction 216) may flow through the truncated conical hollow 214. The conical cylinder funneling surface 212 has a longitudinal axis 202, a proximal intake opening ('cone base') 218 whose internal diameter is D1, and a distal outlet opening whose internal diameter is D2 (where D2<D1). The value of D1 may be, for example, between 8 millimeters and 15 millimeters, which is compliant with typical nostrils. The value of D2 may be about half the value of D1. The FFD 200 may have a length L1 whose value may be, for example, between 10 millimeters and 20 millimeters. The terms 'proximal' and 'distal' refer to a subject's nostril as reference point when the FFD 200 is in use, with 'proximal' being closer to the nostril. Any part of the FFD 200 may be made of a material selected from the group of materials consisting of metal, plastic, and rubber, for example.

The conical cylinder surface 212 is at an angle α relative to longitudinal axis 202 (angle 2α is referred to herein as the 'funneling angle'). The funneling angle 2α may be zero or greater than zero (e.g., 2α=80 degrees). Other funneling angles may be used. The funneling angle 2α may be optimized to obtain a best performance of the FFD 200 as a whole.

The carbon dioxide sampling part 220 may functionally be divided into, or includes, two sections: (1) a $CO_2$ sampling section 222, and (2) an exhaust section 230. The carbon dioxide sampling section 222 includes a $CO_2$ sampling chamber 224 and a $CO_2$ sampling tube 226 through which exhaled $CO_2$ (or exhaled $CO_2$-enriched air) is to be sampled. The carbon dioxide sampling tube 226 is to evacuate a $CO_2$ sample from the $CO_2$ sampling chamber 224 to the outside of the FFD 200. The $CO_2$ sampling tube 226 may include an axial $CO_2$ tube section ("ATS") 228 for collecting exhaled $CO_2$. To this effect, the ATS 228 has an opening 227 facing towards the funnel part 210. The opening 227 of the ATS 228 is referred to herein as ATS 'internal opening' because it resides inside the FFD 200. The carbon dioxide sampling tube 226 may also include a radial $CO_2$ tube section ("RTS") 229. The RTS 229 may be long such that it outwardly protrudes from the $CO_2$ sampling part 220, and its opening (not shown in FIG. 2), which is the other opening of the $CO_2$ sampling tube 226, may be configured to mate with another tube (e.g., a $CO_2$ sampling line) that may be connected to a $CO_2$ monitoring system. The ATS 228 and the RTS 229 are both in fluid flow communication with the $CO_2$ sampling chamber 224. The RTS 229 may be at a right angle with respect to the ATS 228. Angles other than 90 degrees may exist between the ATS 228 and the RTS 229.

The exhaust section 230 includes a gas discharge chamber ("GDC") 250 that functions as an outlet nozzle through which, during operation, a gas mixture, which includes exhaled $CO_2$ (or $CO_2$-enriched air) and gas originating from a gas chamber, or gas reservoir, 270, flows (in direction 240) out of (e.g., cleared from) the FFD 200. The gas chamber 270 may be housed in a peripheral housing 206.

The $CO_2$ sampling part 220 may include an internal conical cylinder (tapering) surface 260 that forms a truncated conical hollow ('frustum' hollow or cavity) that passes through the $CO_2$ sampling part 220. The distal end of the funnel part 210 is connected to, and thus axially and distally 'extended' by a circular, or ring-like shaped, strip ('collar') 211, such that the circular strip 211 'slightly' (e.g., a few millimeters or centimeters) protrudes (extends) into the $CO_2$ sampling section 222 (e.g., into the $CO_2$ sampling chamber 224); e.g., into the truncated conical hollow formed by conical cylinder surface 260. The circular strip 211 is referred to herein as the 'after-funneling extension', or AFE. The AFE 211 and the funnel part 210 may be separate elements that may be mounted on one another (for example, by welding them), or they may be manufactured as one body, for example by molding them as one body.

The conical cylinder surface 260 has a longitudinal axis that may coincide with the longitudinal axis 202, or it may slant slightly (e.g., within ±20 degrees) relative to longitudinal axis 202. The conical cylinder surface 260 has an outlet distal opening 252 whose internal diameter is D4, and an intake proximal opening whose internal diameter D3 is smaller than D4. In addition, the value of D3 may be identical or similar to D2. For example, the value of D3 may be slightly greater than the value of D2 in order to accommodate for the AFE 211.

The conical cylinder surface 260 is at an angle θ relative to the longitudinal axis 202. The angle 2β, which is defined by diameters D3 and D4 and the distance between the intake proximal opening and the outlet distal opening 252 of the conical cylinder surface 260, is referred to herein as the 'exhaust angle'. The exhaust angle 2β may be zero or greater than zero (e.g., 2β may be between approximately 10 degrees and 40 degrees). Other exhaust angles may also be used. The exhaust angle may be optimized to obtain a best performance of the FFD 200 as a whole. The optimization exhaust angle may be, for example, 30 degrees±5 degrees, depending on the structural dimensions (e.g., length, diameter) of the other parts.

The funnel part 210 and the $CO_2$ sampling part 220 may be lengthwise coupled or mounted on one another, or they may be formed (e.g., manufactured) as one body, such that a rounded (e.g., ring-like shaped, or circular) hollow chamber, cavity, or the gas reservoir 270 is formed between them. The hollow chamber 270 includes an intake opening (e.g., intake opening 272) through which a propellant gas (e.g., oxygen) may be provided to the hollow chamber 270 from an external gas source. The external gas source is not shown in FIG. 2.

The funnel part 210 and the $CO_2$ sampling part 220 may be also mounted on one another, or they may be formed (e.g., manufactured) as one body, such that a rounded (e.g., ring-like shaped, or circular) hollow channel (passage) 280 is formed between them. The hollow chamber 270 also includes a rounded (e.g., circular) outlet opening 290 through which the propellant gas stored in the hollow chamber 270 flows (282) from the hollow chamber 270 to the $CO_2$ sampling chamber 224. In operation, pressurized gas is continuously delivered to the hollow chamber 270 (e.g., through the intake opening 272) and, due in part to the gas pressure inside the hollow chamber 270, gas flows into the circular hollow channel 280 which channels the gas, through the circular outlet opening 290, to the $CO_2$ sampling chamber 224, in direction 284.

The AFE 211 forms (in conjunction with internal tapering surface 260 and circular proximal end 292 of the $CO_2$ sampling part 220) the circular outlet opening 290. The AFE 211 forms a circular outlet opening 290 for the hollow channel 280. When gas is provided to the chamber 270 (e.g., through the opening 272) from an external gas source, it is compressed to some degree, and thus pressurizes the chamber 270. As gas is continually provided to the chamber 270, gas forcedly flows from the gas chamber 270 to the $CO_2$ sampling chamber 224 through the circular hollow channel 280 and the opening 292. The circular hollow channel 280 and the opening 292 are narrow (e.g., a few millimeters wide). As a result of this, gas expelled from the chamber 270 is forced to flow into the $CO_2$ sampling chamber 224 in the form of a gas jet (284). Since the gas opening 292 is circular, the gas jet flowing through it (into the $CO_2$ sampling chamber 224) is also circular. The gas jet 284 complies with the Coanda effect, which means that the gas jet 'attaches' itself (it flows close, or adheres) to the cylindrically conical inner surface of the $CO_2$ sampling part 220; namely, to the surface 260, and remains attached to the surface 260 even though the surface 260 may deviate from the initial direction of the gas jet exiting the opening 290. (The gas jet expelled through the opening 290 is schematically shown at 284 attached to the surface 260.)

The gas chamber 270 may, in general, lengthwise be peripherally positioned anywhere on the FFD 200. For example, the gas chamber 270 may be structured such that it is peripheral to the $CO_2$ sampling part 220. The gas chamber 270 and the $CO_2$ sampling chamber 224 (or the GDC 250) may be concentric. Alternatively, the gas chamber 270 may be structurally peripheral to the funnel part 210. Alternatively, part of the gas chamber 270 may be structurally peripheral to the $CO_2$ sampling part 220 and part of the gas chamber 270 may be structurally peripheral to the funnel part 210.

In operation, the FFD 200 is placed near a patient's nostril. When the patient exhales, some $CO_2$ flows (216) into the funnel part 210. The gas jet reshaped in the FFD 200 by the Coanda effect helps drawing more of the exhaled $CO_2$ into and through the FFD 200 (thanks to the Venturi effect), and, in addition, the gas jet helps boosting and directing the $CO_2$ flow in the $CO_2$ sampling chamber 224 such that more $CO_2$ is forced to flow into the $CO_2$ sampling tube 226.

The AFE 211 and the $CO_2$ sampling chamber 224 may be shaped such that the $CO_2$ drawing and flow reshaping effect is optimal, for example in the sense that most (preferably all) of the exhaled $CO_2$ (or $CO_2$-enriched air) that enters the FFD 200 flows into the intake opening 227 of the $CO_2$ sampling tube 228 and, at the same time, interfering gas turbulences at, or near, axial $CO_2$ sampling tube 228, and in particular in front of the intake opening 227, are minimized or subsides.

The diameter of the inner truncated conical surface 260 of the $CO_2$ sampling part 220 positioned lengthwise in the middle of the $CO_2$ sampling part 220 is about $0.5 \times (D3+D4)$. The diameter values D1 and D2 of the intake opening 218 and the outlet opening 290, respectively, of the funnel part 210 and the length between these two openings are selected such that they facilitate flow of an effective amount of the exhaled $CO_2$ (or $CO_2$-entiched air) into the FFD 200.

Diameter d1 of the $CO_2$ sampling tube 226 may be selected such that, in the one hand, the $CO_2$ sampling tube 226 does not interfere much with the flow of gases through the FFD 200, and, on the other hand, d1 is large enough to enable an effective amount of $CO_2$ (or $CO_2$-enriched air) to enter the $CO_2$ sampling tube 226 through the intake opening 227. The value d1 of $CO_2$ sampling tube 226 may be selected to be in compliance with a standard tube that is used for sampling $CO_2$. For example, the value of d1 may be 1 millimeter or about 1 millimeter. "Effective amount of $CO_2$" (or $CO_2$-enriched air) means an amount of sampled $CO_2$ (or $CO_2$-entiched air) that is sufficient for measuring concentration level of $CO_2$ samples by an external $CO_2$ monitoring system. The value of d1 may be, for example in some embodiments, one third, or so, of the average inner diameter of $CO_2$ sampling part 220. For example, d1 may be equal to $0.30$ times $(D3+D4)/2$, or so, though other ratios (between d1, D3, and D4) may be used.

Figure 2B:
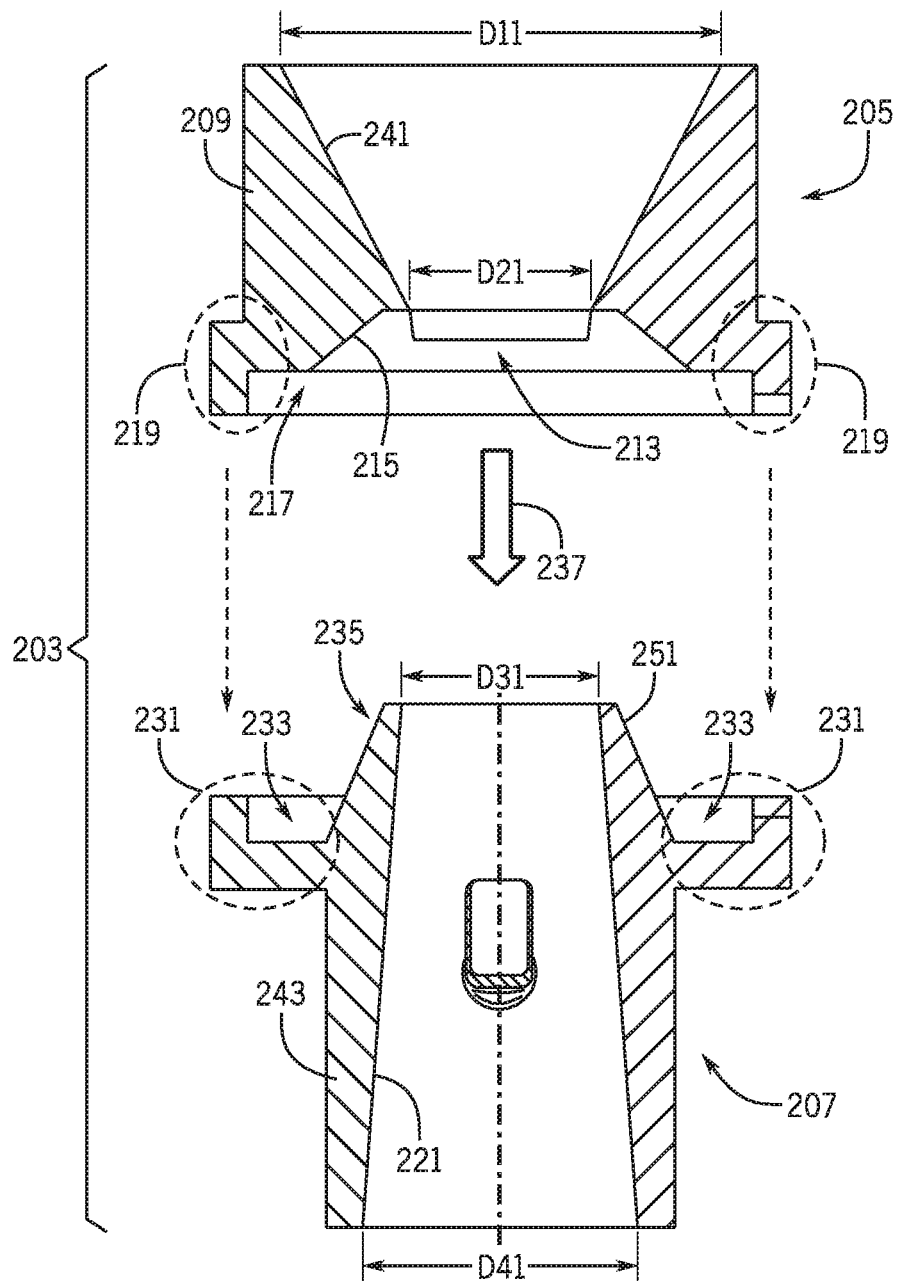
FIG. 2B shows an exploded view of a FFD according to an example embodiment.

Internal surface 260 of $CO_2$ sampling part 220 may open linearly, as exemplified by FIG. 2, or nonlinearly. For example, the generatrix of the internal surface 260 of the $CO_2$ sampling part 220 may be curved. The "generatrix" as used herein is a line segment between the apex of a cone and a point in the perimeter of the base of the cone. The line segment 'produces' a lateral surface (the cone's surface) when it is 'moved' in a certain manner. The FFD 200 may be manufactured (e.g., molded) as two, separate, parts that may be assembled (as demonstrated in FIG. 2B), or as one body).

FIG. 2B shows a method for assembling a FFD 203 that may be identical or similar to the FFD 200 of FIG. 2A, according to an example embodiment. The FFD 203 may include two main parts: a funneling part 205 identical or similar to the funneling part 210 of FIG. 2A, and a $CO_2$ sampling part 207 identical or similar to the $CO_2$ sampling part 220 of FIG. 2A.

The funneling part 205 may include a generally cylindrical body 209 that may include an internal conical cylinder funneling surface 241 similar to the conical cylinder funneling surface 212. The funneling surface 241 tapers distally. The funneling part 205 may also include an internal lengthwise conical hollow 213 that is in fluid flow communication with the funneling surface 241. The conical hollow 213 has a distally widening conical cylinder funneling surface 215. The funneling part 205 may also include an internal hollow space 217 that is distal to, and in fluid flow communication with, the conical hollow 213. The funneling part 205 may also include a distal peripheral mounting 'L'-shaped member 219. In some embodiments, as exemplified by FIG. 2B, the peripheral 'L'-shaped member 219 defines an internal, 'disc' like, hollow 217.

The $CO_2$ sampling part 207 may include a generally cylindrical body 243 that includes an internal conical cylinder surface 221 identical or similar to the internal conical cylinder (tapering) surface 260 in FIG. 2A. Like the surface 260 in FIG. 2A, the surface 221 forms a truncated conical hollow ('frustum' hollow or cavity) that passes through the $CO_2$ sampling part 207. The conical cylinder surface 221 widens distally. The $CO_2$ sampling part 207 may also include a peripheral mounting 'L'-shaped member 231. In some embodiments, as exemplified by FIG. 2B, the peripheral 'L'-shaped member 231 may radially protrude from the cylindrical body 243 and define, in conjunction with the cylindrical body 243, a circular, ring-like, open channel 233.

A proximal section of the cylindrical body 243 may have a tapering end 235 that proximally tapers away from the 'L'-shaped member 231 (or from the open channel 233), and into the conical hollow 213 of the funneling part 205.

The tapering end 235, the hollow space 217, the conical hollow space 213, and the funneling surface 215 are designed such that, when the funneling part 205 is mounted (237) on the $CO_2$ sampling part 207 (e.g., by mounting the 'L'-shaped member 219 to or on a 'L'-shaped member 231 in an airtight way), the circular channel 233 and the hollow 217 of the funneling part 205 jointly form, or define, a circular gas chamber identical or similar to the gas chamber 270 of FIG. 2A, and slanting surface 251 of the tapering end 235 and the slanting surface 215 jointly form, or define, a hollow channel (passage) and a channel opening that are respectively identical or similar to the hollow channel (passage) 280 and the channel opening 290 in FIG. 2A. 'L'-shaped mounting member 231 of the $CO_2$ sampling part 207 and the cylindrical body 243 jointly form an open ring-like channel (e.g., the open channel 233) that engages the internal hollow space 217 when the parts 205 and 207 are assembled.

The 'L'-shaped member 219 may be mounted, connected or attached to the 'L'-shaped member 231 in an airtight way by, for example, welding them together, or by gluing them. 'Airtight,' as used herein, means in a way that makes the resulting gas chamber (e.g., the gas chamber 270) impervious to external gases and prevents pressurized gas in the gas chamber 270 from 'peripherally' escaping the gas chamber 270 between the 'L'-shaped member 219 and the 'L'-shaped member 231. It is noted that, during operation of the FFD 203, gas normally flows from the gas chamber (e.g., the gas chamber 270) into the $CO_2$ sampling chamber of the FFD (e.g., the $CO_2$ sampling chamber 224).)

The tapering end (235) of the $CO_2$ sampling part 207 is designed such that, when the parts 205 and 207 are assembled, the tapering portion of $CO_2$ sampling part 207 enters the hollow space 213 of the funneling part 205, to thus facilitate creation of: the ring-shaped gas chamber (e.g., a gas chamber similar to the gas chamber 270), the circular hollow channel or passage (e.g., a hollow channel or passage similar to the circular hollow channel 280), and the circular opening (e.g., a circular opening similar to the opening 290). The values of D11, D21, D31 and D41 in FIG. 2B may be identical or similar to the values of D1, D2, D3 and D4 in FIG. 2A, and selected in the way described in connection with FIG. 2A.

FIG. 3A depicts a cross-sectional view of a three-dimensional FFD 300 according to an example embodiment. The FFD 300 includes a funneling part 310 and a $CO_2$ sampling part 320. A peripheral gas chamber is shown at 370. The FFD 300 includes a $CO_2$ sampling tube that may include an axial $CO_2$ sampling tube 328 for sampling $CO_2$ (or $CO_2$-enriched air), and a radial $CO_2$ sampling tube 329 for transferring the $CO_2$ (or $CO_2$-enriched air) samples to an external $CO_2$ monitoring system. The $CO_2$ tubes 328 and 329 may be one, or form the same, tube that samples $CO_2$ (or $CO_2$-enriched air) and transfer $CO_2$ samples to an external $CO_2$ monitoring system.

In some embodiments, a gas FFD (200, 203) is disclosed for sampling exhaled gases. The FFD may include a funneling part (210, 205) that may be configured to receive and funnel exhaled $CO_2$-enriched air, and a $CO_2$ sampling part (220, 207) that is in fluid flow communication with the funneling part (210, 205). The $CO_2$ sampling part (220, 207) may include a $CO_2$ sampling chamber 224 to receive the $CO_2$-enriched air, and a $CO_2$ sampling tube 226, which is located in the $CO_2$ sampling chamber 224, to evacuate a $CO_2$ sample from the $CO_2$ sampling chamber 224 to the outside of the FFD. The $CO_2$ sampling tube 226 may include an axial $CO_2$ tube section 228 that may be centered in the $CO_2$ sampling chamber 224. The funneling part (210, 205) and the $CO_2$ sampling part (220, 207) may have a common longitudinal axis, and they may form a gas chamber (e.g., the gas chamber 270) between them, to contain a propellant gas, and a hollow channel 280 to channel the propellant gas from the gas chamber 270 into and through the $CO_2$ sampling chamber 224. The $CO_2$ sampling part (220, 207) may also include a gas exhaust section 230.

Each of the funneling part (210, 205) and the $CO_2$ sampling part (220, 207) may include an 'L'-shaped mounting member (219, 231). The $CO_2$ sampling part 207, for example, may include a cylindrical body 243, and the 'L'-shaped mounting member 231 of the $CO_2$ sampling part 207 and the cylindrical body 243 may jointly form a ring-like channel 233. The cylindrical body 243 of the $CO_2$ sampling part 207 may include a tapering end 235. The funneling part 205 may include a conical hollow space 213 that is configured to mate with the tapering end 235 of the $CO_2$ sampling part 207, to thus form the hollow channel 280.

The funneling part (210, 205) may include an AFE 211 that may protrude into the $CO_2$ sampling chamber 224. The AFE 211 may form a circular outlet opening 290 for the hollow channel 280, so that a gas flowing from the gas chamber (270) flows into the $CO_2$ sampling chamber in the form of a gas jet 284.

FIG. 3B depicts the FFD 300 of FIG. 3A in full, from a different perspective, and shows the external part of the $CO_2$ tube 329 and a gas intake 372 through which a propellant gas may be provided to the gas chamber 370 from an external gas source. The propellant gas may be oxygen, or another gas.

Figure 4:
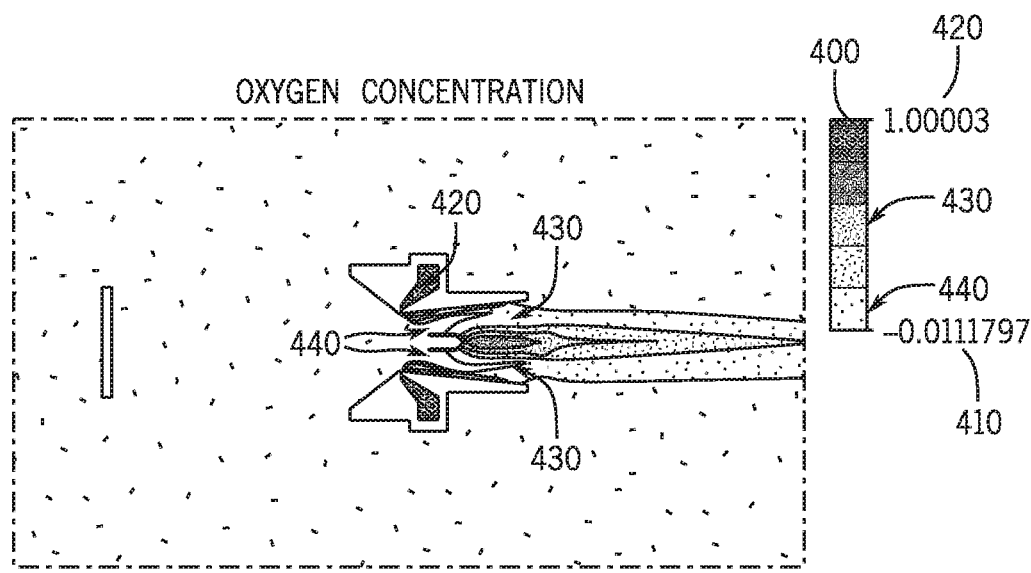
FIG. 4 depicts simulated oxygen flow in a FFD according to an example embodiment.

FIG. 4 depicts a simulation of oxygen flow in a FFD (e.g., FFD 200, 300) according to an example embodiment. Oxygen was used as an example propellant gas, but other gases may be used for this function. Bar 400 shows oxygen concentration level between a lowest concentration level 410 and a highest oxygen concentration level 420.

Oxygen was provided into a gas chamber of a FFD similar to gas chamber 270 (FIG. 2A) or gas chamber 370 (FIG. 3A), and forced to flow into a $CO_2$ sampling part of the FFD. Since the oxygen pressure is maximum inside the gas chamber of the FFD, its concentration level is maximum in at this location (e.g., represented by 420) and, therefore, is the highest oxygen concentration level 420 in bar 400.

Compliant with the Coanda effect, the oxygen flowing out of the gas chamber and into the $CO_2$ sampling chamber adheres to ('follows') the internal widening surface of the $CO_2$ sampling part. The lighter less saturated grey areas in FIG. 4A show oxygen flow. As oxygen flows outside the gas chamber, its pressure, and hence the oxygen concentration level, lowers (e.g., approaches concentration level 410). The lowered oxygen concentration level is represented by 430 in bar 400 and in the image, and represents an oxygen concentration level between the lowest oxygen level 410 and the maximum oxygen level 420. The oxygen concentration level in the FFD is relatively high (e.g., represented by 420) near the outlet nozzle walls, in the exhaustion section of the FFD, on the right hand side of the image, and relatively low (as represented by 440) near the $CO_2$ sampling tube (in the middle of the $CO_2$ sampling part of the FFD). The concentration level 440 in the bar 400 and in the image represents a very low oxygen concentration level. FIG. 4 demonstrates an advantage of the Coanda effect, which is that in the area near the $CO_2$ sampling tube the oxygen concentration level is very low (this is represented by 440), which is important in order to mitigate dilution ('contamination') of $CO_2$ samples by oxygen. Dilution of $CO_2$ samples results in inaccurate and unreliable $CO_2$ measurements.

Figure 5:
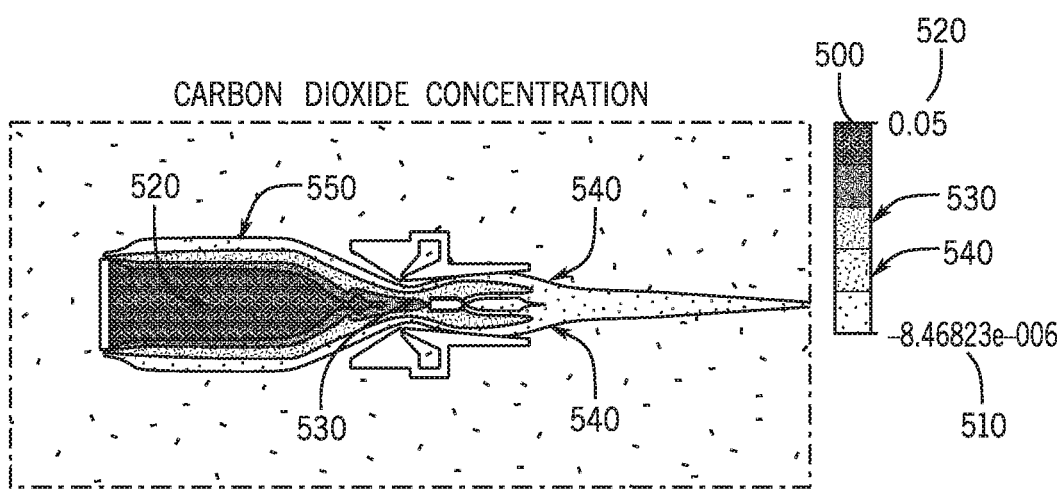
FIG. 5 depicts simulated exhaled $CO_2$-enriched air flow in a FFD according to an example embodiment.

FIG. 5 depicts simulation of exhaled $CO_2$-enriched air flow in a FFD (e.g., FFD 200, 300) according to an example embodiment. Bar 500 shows $CO_2$ concentration levels between a lowest concentration level 510 and a highest $CO_2$ concentration level 520.

$CO_2$ enriched air was provided to a $CO_2$ funneling part of a FFD. The $CO_2$ concentration level in front of the $CO_2$ funneling part is maximum and, therefore, represented by the concentration level 520 in bar 500 and in the image. As $CO_2$-enriched air flows in the $CO_2$ funneling part and towards the $CO_2$ sampling tube, its concentration level lowers, though it remains relatively high. The lowered $CO_2$ concentration level near the intake part of the $CO_2$ sampling tube is represented by concentration level 530 in the bar 500 and in the image. The concentration level 530 represents a relatively high $CO_2$ concentration level in the bar 500. The $CO_2$ concentration level is further lowered as the $CO_2$ flows past the $CO_2$ sampling tube. The $CO_2$ concentration level in the area 'behind' the $CO_2$ sampling tube is represent by 540. 'Behind the $CO_2$ sampling tube' is the area in the $CO_2$ sampling part that is opposite to the intake side of the $CO_2$ sampling tube.

FIG. 5 demonstrates another advantage of the Coanda effect, which is that the $CO_2$-enriched air flow 'splits', or 'spans out,' before it reaches the $CO_2$ sampling tube, and follows the internal surface of the $CO_2$ sampling part of the FFD in compliance with the Coanda effect. As a result of the $CO_2$-enriched air flow being split, the periphery portion of the $CO_2$-enriched air flow (which is shown at 550), which has a relatively low concentration level 540, is drawn to the internal surface of the $CO_2$ sampling part of the FFD. The $CO_2$-enriched air flow drawn to the internal surface of the $CO_2$ sampling part is shown, in FIG. 5, as two horizontal 'prong'-like bright areas that extend to the right hand side of the image. As a result of the $CO_2$-enriched air flow being drawn sideways, $CO_2$-enriched air having a relatively high $CO_2$ concentration level flows in the center of (and focused in) the $CO_2$ sampling part towards the $CO_2$ sampling tube's intake part.

FIGS. 4 and 5, thus, demonstrate that even though oxygen (as an example propellant gas) is forced to flow into the $CO_2$ sampling chamber of the FFD in order to draw more of the exhaled $CO_2$-enriched air flow into the FFD, the oxygen does not interfere with (it does not dilute) the $CO_2$ samples entering the $CO_2$ sampling tube.

Figure 6:
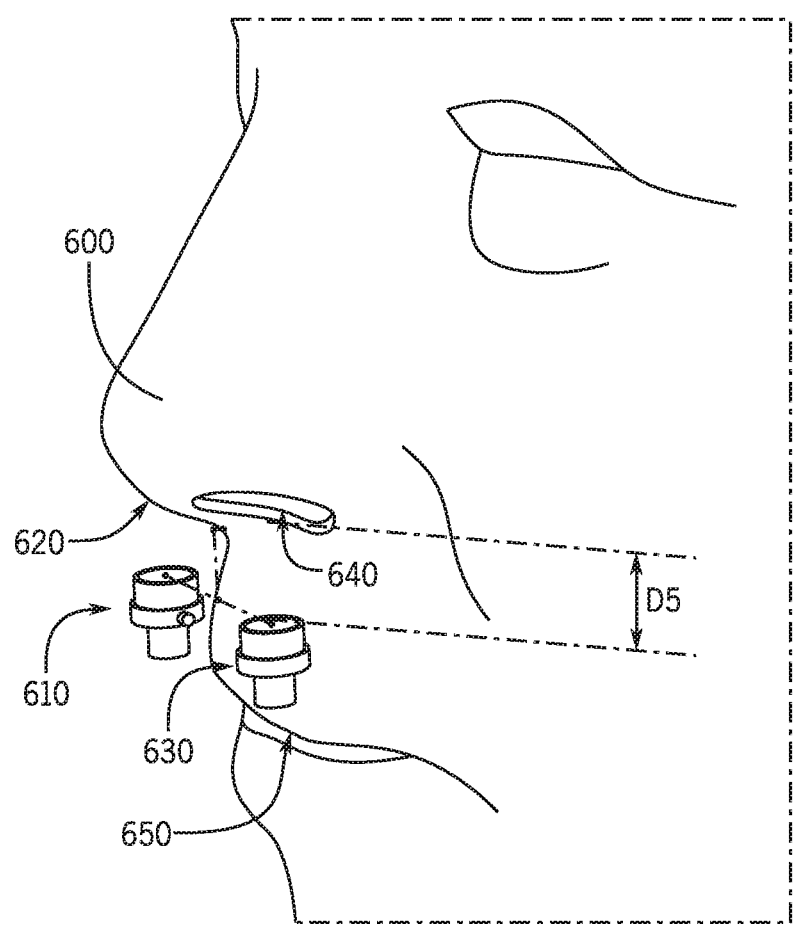
FIG. 6 depicts location of two FFDs relative to a subject's nose according to an example embodiment.

FIG. 6 depicts location of two FFDs relative to a subject's nose 600 according to an example embodiment. A first FFD 610 is placed near a first nostril 620, and a second FFD 630 is placed near a second nostril 640. Each FFD is to be distanced a distance D5 from the respective nostril in order to allow a subject to breath in and breath out without the exhaled $CO_2$-enriched air and the breathed-in air or oxygen interfering with one another. The value of D5 may be selected to be within a range of approximately 5-15 millimeters, and, in any case, it has to be selected such that the FFDs 610 and 630 are positioned between upper lip 650 of the subject and the nostrils 620 and 640.

Figure 7A:
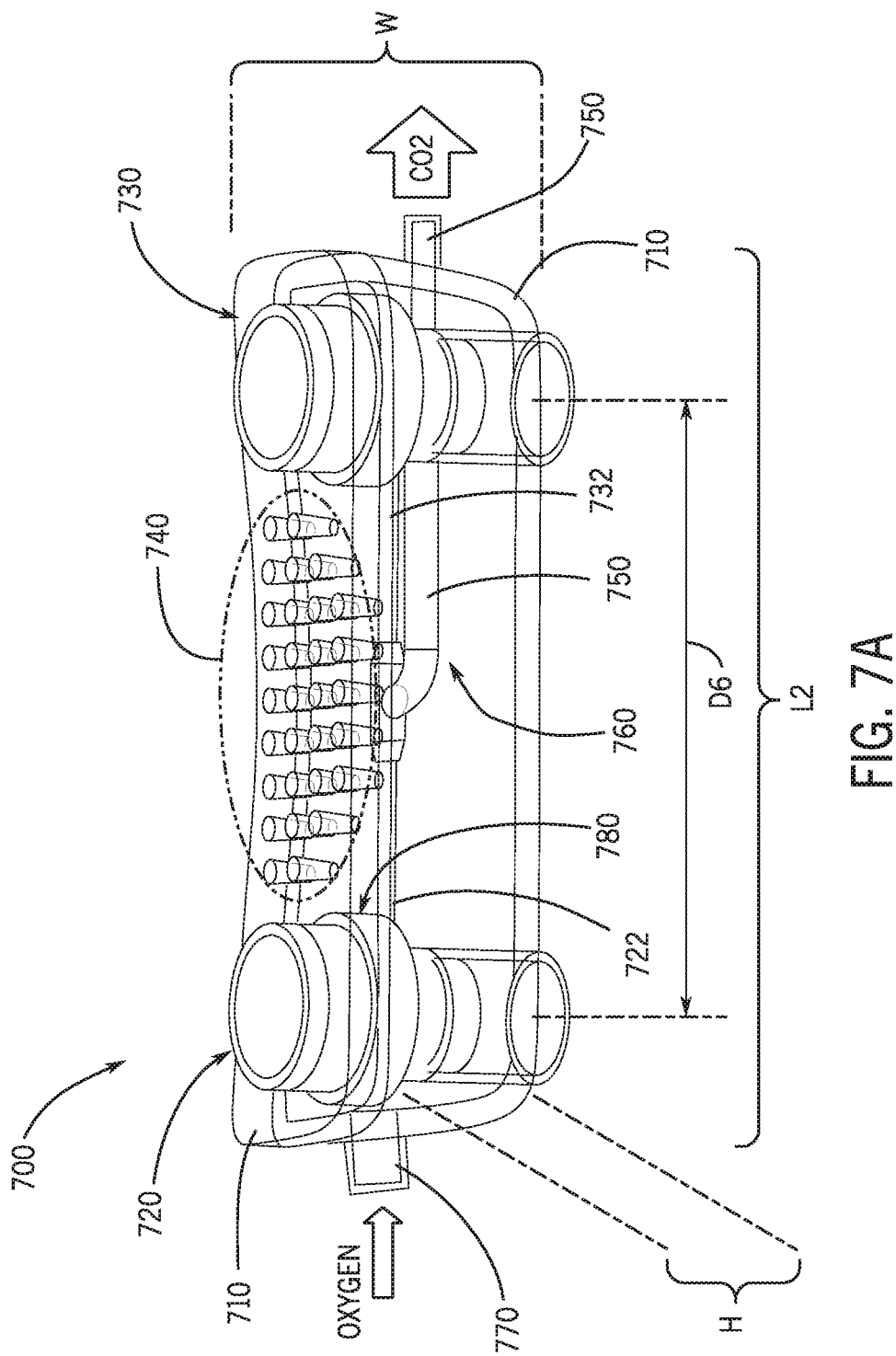
FIG. 7A shows a prong-free cannula according to an example embodiment.
Figure 7B:
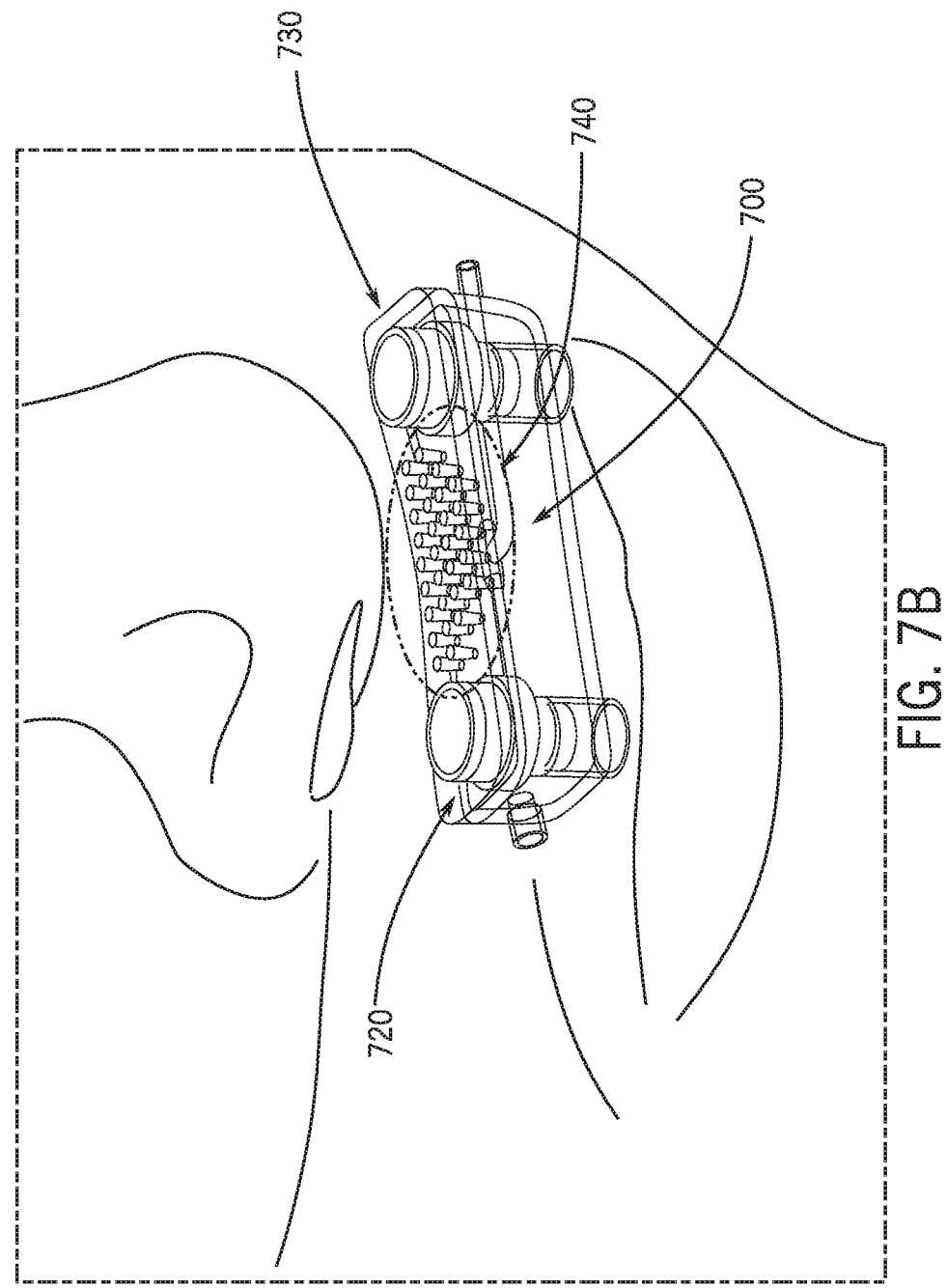
FIG. 7B depicts the prong-free cannula of FIG. 7A positioned adjacent to a subject's nose.

A prong-free cannula (PFC) incorporating two FFDs is shown in FIG. 7A and in FIG. 7B, which are described below. In some embodiments, a PFC 700 may include a first gas FFD 720 and a second gas FFD 730 to sample $CO_2$-enriched air exhaled by a subject. The PFC 700 may also include a cannula body 710 that may include the first gas FFD 720, the second gas FFD 730, and, in addition (as an option), a plurality of apertures 740 for providing, there through, oxygen to a subject during inhalation. Each of the first gas FFD 720 and the second gas FFD 730 may include the elements described herein.

The PFC 700 may also include a $CO_2$ sampling line 750 that may be connected to the $CO_2$ sampling tube 226 of each of the first and second gas flow-focusing devices 720 and 730, respectively, and, in addition, an oxygen manifold 760 that is in fluid flow communication with the plurality of apertures 740 and with the gas chamber 270 of (in) each gas flow-focusing device 720, 730. The $CO_2$ sampling line 226 may connect each $CO_2$ sampling tube 226 of the FFDs 720, 730 to an external $CO_2$ monitoring system. The PFC 700 may be used only for sampling exhaled $CO_2$, or only for providing oxygen to a subject, or for both functions. The PFC 700 may also include an oxygen line 770 for providing oxygen both to the plurality of apertures 740 and to the gas intake opening of the gas chamber 270 of (in) each FFD 720, 730.

Referring again to FIG. 7A, example PFC 700 includes a cannula body 710. The cannula body 710 has a length L2, a width W and a thickness H that are selected so as to accommodate the first FFD 720, the second FFD 730 that is lengthwise distanced a distance D6 from the first FFD 720, and the plurality of oxygen apertures 740, slits or through holes that are interposed between the first FFD 720 and the second FFD 730. The cannula body 710 may be made of metal, plastic, or rubber, or any combination thereof. The value of D6 may be an average distance between centers of the nostrils 620, 640 (e.g., D6=15 millimeters). The value of D6 may be within the range of, for example, approximately 5-20 millimeters.

The cannula body 710 includes a $CO_2$ sampling tube 722 through which $CO_2$ samples flow out of the FFD 720, and a $CO_2$ sampling tube 732 through which $CO_2$ samples flow out of the FFD 730. The $CO_2$ sampling tube 722 and the $CO_2$ sampling tube 732 are connected to a $CO_2$ sampling line 750 (e.g., by a 'T'-like tube connector) through which $CO_2$ sampled by the two FFDs 720, 730 further flows to an external $CO_2$ monitoring system. The $CO_2$ sampling tubes 722 and 732 and the $CO_2$ sampling line 750 are in fluid flow communication. The cannula body 710 also includes an oxygen manifold 760 (e.g., a chamber) that is connected to an external oxygen supply line 770. In operation, oxygen is provided, through oxygen supply line 770, to the oxygen manifold 760, and dispersed through the plurality of apertures 740 such that small oxygen jets flowing out through the plurality of apertures 740 create an oxygen 'cloud' between the PFC 700 and the subject's nose for the subject to breath in. The number, size (e.g., diameter) and distribution of the plurality of apertures 740 in the PFC 700 may be selected in a way that reduces or minimizes the oxygen dilution effect; namely, in a way that reduces or minimizes the amount of oxygen that mixes with the exhaled $CO_2$-enriched air flowing into the FFDs 720 and 730.

The values of L2, W and H are also selected so as to accommodate for the $CO_2$ sampling tubes 722 and 732, the $CO_2$ sampling line 750 and the oxygen manifold 760. The value of H may be smaller than the length of the FFDs 720 and 730, such that the cannula body 710 includes (accommodates) only a portion (e.g., a middle third) of the length of the FFDs 720 and 730. Alternatively, the value of H may be large enough to completely include or contain the FFDs 720 and 730.

At 780 is shown a propellant gas intake opening of the FFD 720. The FFD 730 also includes a propellant gas intake opening, though it is not referenced in FIG. 7A. Propellant gas intake openings are shown more clearly in FIG. 2A (opening 272), and in FIG. 3B (opening 372). The propellant gas intake opening 780 and the propellant gas intake opening of the FFD 730 are in fluid flow communication with the oxygen manifold 760. Therefore, oxygen contained in the oxygen manifold 760 also flows into these openings, and thus used as propellant gas in the FFDs 720 and 730. FIG. 7B shows the PFC 700 of FIG. 7A positioned adjacent to a subjects nose, as would be the case when the PFC is in operation.

FIG. 8 depicts simulation of $CO_2$ flow flowing from a subject nose towards, and around, two flow-focusing devices according to an example embodiment. As FIG. 8 demonstrates, a high concentration $CO_2$ level is shown in the $CO_2$ flow 810 flowing from nostril 820 to FFD 830, and a high concentration $CO_2$ level is also shown in the $CO_2$ flow 840 flowing from nostril 850 to FFD 860. FIG. 8 also demonstrates that the two $CO_2$ flows 810 and 840 are separate, with no mutual interference.

FIG. 9 depicts a PFC 900 that includes a first FFD 910, a second FFD 920, a gas manifold 930 to which oxygen (as an example propellant gas) is provided through oxygen line 940. Other parts of the PFC 900 are not referenced in FIG. 9. FIG. 9 also depicts simulated oxygen flow from the PFC 900 towards the subject nostrils. Since oxygen is forced into the gas manifold 930, its concentration level in the gas manifold 930 is relatively high (e.g., concentration level 960). As oxygen flows out through the multiple gas apertures, its concentration level (e.g., concentration level 970)

gets lower, so the concentration level 970 representing it shown in bar 950 is lower than concentration level 960 in bar 950. As demonstrated by FIG. 9, the oxygen between the two nostrils, at area 980, is characterized by having high concentration level 970, and the oxygen between each nostril and the respective FFD 910, 920, for example at area 990, is characterized by having low concentration level 992.

Figure 10:
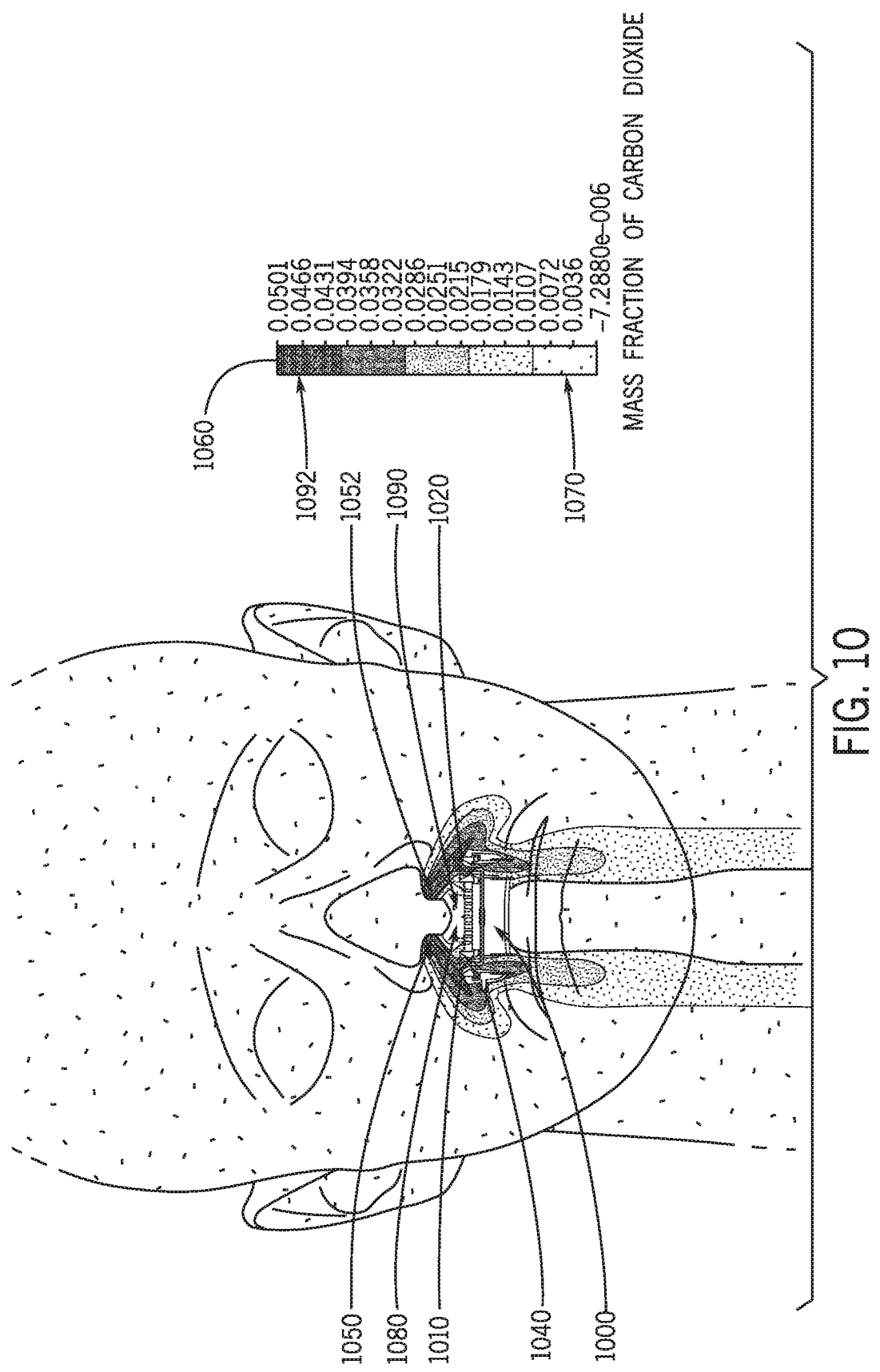
FIG. 10 depicts a cannula with prongs and an internal septum, whereby one nasal prong samples CO.sub.2 from a subject's breath and another nasal prong delivers oxygen to the subject.

FIG. 10 depicts a PFC 1000 that includes a first FFD 1010, a second FFD 1020, a gas manifold to which oxygen (as an example propellant gas) is provided through an oxygen line 1040. Other parts of the PFC 1000 are not referenced in FIG. 10. FIG. 10 also depicts simulated $CO_2$ flow from nostril 1050 to FFD 1010 and from nostril 1052 to FFD 1020. As demonstrated by FIG. 10, the $CO_2$ between the two nostrils 1050, 1052, for example at area 1080, is characterized by having a low concentration level 1070 in bar 1060, and the $CO_2$ between each nostril 1050, 1052 and the respective FFD 1010, 1020 is characterized by having a high concentration level 1092.

The PFC device of the present disclosure may be used, for example, for sampling $CO_2$ by using oxygen as a propellant gas. However, the scope of the present disclosure is not limited in this regard. For example, the PFC device may be used to sample another gas (for example a metabolic waste gas, a waste gas indicative of or characterizing certain physiological state or condition of a subject, or a certain pathology, etc.) in the gases mixture that a subject may exhale and/or the propellant gas may be a gas other than oxygen.

Sub-aspects of some individual embodiments may be used with other embodiments. While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

The invention claimed is:

1. A gas flow-focusing device for sampling exhaled gases, comprising:
a funneling part configured to receive and funnel exhaled carbon dioxide ($CO_2$)-enriched air; and a $CO_2$ sampling part in fluid flow communication with the funneling part, the $CO_2$ sampling part comprising:
a $CO_2$ sampling chamber configured to receive the $CO_2$-enriched air, and a $CO_2$ sampling tube located in the $CO_2$ sampling chamber,
wherein the funneling part and the $CO_2$ sampling part have a common longitudinal axis and form:
a gas chamber between the funneling part and the $CO_2$ sampling part to contain a propellant gas, and
a hollow channel configured to channel the propellant gas from the gas chamber into and through the $CO_2$ sampling chamber.

2. The gas flow-focusing device of claim 1, wherein the $CO_2$ sampling part comprises a gas exhaust section.

3. The gas flow-focusing device of claim 1, wherein the $CO_2$ sampling tube is configured to evacuate a $CO_2$ sample from the $CO_2$ sampling chamber to the outside of the flow-focusing device.

4. The gas flow-focusing device of claim 1, wherein each of the funneling part and the $CO_2$ sampling part includes an 'L'-shaped mounting member.

5. The gas flow-focusing device of claim 4, wherein the $CO_2$ sampling part comprises a cylindrical body, and wherein the 'L'-shaped mounting member of the CO2 sampling part and the cylindrical body jointly form a ring-like channel.

6. The gas flow-focusing device of claim 5, wherein the cylindrical body of the $CO_2$ sampling part comprises a tapering end.

7. The gas flow-focusing device of claim 6, wherein the funneling part comprises a conical hollow space-, the conical hollow space is-configured to mate with the tapering end of the $CO_2$ sampling part-, to thus form the hollow channel.

8. The gas flow-focusing device of claim 1, wherein the funneling part comprises an after-funneling extension protruding into the $CO_2$ sampling chamber.

9. The gas flow-focusing device of claim 8, wherein the after-funneling extension forms a circular outlet opening for the hollow channel.

10. The gas flow-focusing device of claim 1, wherein the $CO_2$ sampling tube comprises an axial $CO_2$ tube section, the axial $CO_2$ tube section being centered in the $CO_2$ sampling chamber.

11. A prong-free cannula comprising:
a first gas flow-focusing device and a second gas flow-focusing device configured to sample carbon dioxide ($CO_2$)-enriched air exhaled by a subject; and
a cannula body including the first gas flow-focusing device, the second gas flow-focusing device, and a plurality of apertures for providing oxygen to the subject during inhalation,
wherein each of the first gas flow-focusing device and the second gas flow-focusing device comprises:
a funneling part configured to receive and funnel exhaled $CO_2$-enriched air; and
a $CO_2$ sampling part in fluid flow communication with the funneling part, the $CO_2$ sampling part comprising:
a $CO_2$ sampling chamber configured to receive the $CO_2$-enriched air, and a $CO_2$ sampling tube located in the $CO_2$ sampling chamber,
wherein the funneling part and the $CO_2$ sampling part have a common longitudinal axis and form:
a gas chamber between the funneling part and the $CO_2$ sampling part configured to contain a propellant gas, and
a hollow channel configured to channel the propellant gas from the gas chamber into and through the $CO_2$ sampling chamber-.

12. The prong-free cannula of claim 11, further comprising:
a $CO_2$ sampling line connected to the $CO_2$ sampling tubes of the first and second gas flow-focusing devices; and
an oxygen manifold in fluid flow communication with the plurality of apertures and with the gas chamber in each gas flow-focusing device.

13. The prong-free cannula of claim 11, wherein the each $CO_2$ sampling part comprises a gas exhaust section.

14. The prong-free cannula of claim 11, wherein each $CO_2$ sampling tube is configured to evacuate a $CO_2$ sample from the respective $CO_2$ sampling chamber to the outside of the respective flow-focusing device.

15. The prong-free cannula of claim 11, wherein each of the funneling part and the $CO_2$ sampling part for each gas flow-focusing device includes an 'L'-shaped mounting member.

16. The prong-free cannula of claim 15, wherein the $CO_2$ sampling part for each gas flow-focusing device comprises a cylindrical body, and wherein the 'L'-shaped mounting member of the $CO_2$ sampling part for each gas flow-focusing device and the respective cylindrical body jointly form a ring-like channel.

17. The prong-free cannula of claim 16, wherein the cylindrical body of the $CO_2$ sampling part for each gas flow-focusing device comprises a tapering end.

18. The prong-free cannula of claim 17, wherein the funneling part for each gas flow-focusing device comprises a conical hollow space, the conical hollow space configured to mate with the respective tapering end of the $CO_2$ sampling part for each gas flow-focusing device, to thus form the hollow channel.

19. The prong-free cannula of claim 18, wherein the funneling part for each gas flow-focusing device comprises an after-funneling extension protruding into the respective $CO_2$ sampling chamber.

20. The prong-free cannula of claim 11, wherein the $CO_2$ sampling tube for each gas flow-focusing device comprises an axial $CO_2$ tube section, the axial $CO_2$ tube section being centered in the respective $CO_2$ sampling chamber.

21. A gas flow-focusing device for sampling exhaled gases, comprising:
   a funneling part configured to receive and funnel exhaled carbon dioxide ($CO_2$)-enriched air; and a $CO_2$ sampling part, comprising:
   a $CO_2$ sampling chamber configured to receive the CO2-enriched air; and
   a $CO_2$ sampling tube located in the $CO_2$ sampling chamber and configured to evacuate a $CO_2$ sample from the $CO_2$ sampling chamber to the outside of the gas flow-focusing device, wherein the funneling part and the $CO_2$ sampling part form:
   a gas chamber between the funneling part and the $CO_2$ sampling part to contain a propellant gas, and
   a hollow channel configured to channel the propellant gas from the gas chamber into and through the $CO_2$ sampling chamber.

* * * * *